US009311451B2

(12) United States Patent
Bae et al.

(10) Patent No.: US 9,311,451 B2
(45) Date of Patent: Apr. 12, 2016

(54) MEDICATION DISPENSING APPARATUS FOR PREVENTING MEDICATION DISPENSING ERROR

(71) Applicant: INFOPIA CO., LTD., Anyang-si (KR)

(72) Inventors: Byeong-Woo Bae, Anyang-si (KR); Keun-Young Kim, Seoul (KR)

(73) Assignees: LCK Co., Ltd., Anyang-si (KR); Jilin Province LongChuang Medical Treatment Technology Co., Ltd., Changchun (CN)

( * ) Notice: Subject to any disclaimer, the term of this patent is extended or adjusted under 35 U.S.C. 154(b) by 136 days.

(21) Appl. No.: 13/948,500

(22) Filed: Jul. 23, 2013

(65) Prior Publication Data

US 2014/0236349 A1 Aug. 21, 2014

(30) Foreign Application Priority Data

Feb. 18, 2013 (KR) .......................... 10-2013-0017092
Feb. 18, 2013 (KR) .......................... 10-2013-0017094

(51) Int. Cl.
*G06K 9/00* (2006.01)
*G06F 19/00* (2011.01)
*B65B 35/44* (2006.01)
(Continued)

(52) U.S. Cl.
CPC .............. *G06F 19/3462* (2013.01); *B65B 1/06* (2013.01); *B65B 1/46* (2013.01); *B65B 35/44* (2013.01); *B65B 57/14* (2013.01); *B65B 57/20* (2013.01)

(58) Field of Classification Search
CPC .................................................. G06F 19/3462

USPC ........................................................ 700/236
See application file for complete search history.

(56) References Cited

U.S. PATENT DOCUMENTS 6,535,637 B1* 3/2003 Wootton et al. ............... 382/190
2006/0124656 A1* 6/2006 Popovich, Jr. ..................... 221/9
(Continued)

FOREIGN PATENT DOCUMENTS

JP 9-253163 A 9/1997
JP 2010-149894 A 7/2010
(Continued)

OTHER PUBLICATIONS

European Search Report mailed Feb. 20, 2015 in counterpart European Application No. 13 18 0216.7 (3 pages, in English).

*Primary Examiner* — Stephen R Koziol
*Assistant Examiner* — Delomia L Gilliard
(74) *Attorney, Agent, or Firm* — NSIP Law

(57) ABSTRACT

A medication dispensing apparatus for preventing a medication dispensing error is provided. The medication dispensing apparatus includes: a communication unit configured to communicate with a manager server; a medication collecting unit configured to contain capsules or tablets for one dose which are discharged from cartridges; a medication image acquiring unit configured to acquire an image of the capsules or tablets contained in the medication collecting unit; and a control unit configured to comprise a dispensing information delivery unit to transmit to the manager server the medication information acquired by the medication image acquiring unit, and a dispensing control unit to continue a medication dispensing process or control capsules or tablets to be re-dispensed according to a user's dispensing control instruction received from the manager server. Accordingly, it is possible to prevent a medication dispensing error.

14 Claims, 18 Drawing Sheets

(51) Int. Cl.
*B65B 57/14* (2006.01)
*B65B 1/06* (2006.01)
*B65B 1/46* (2006.01)
*B65B 57/20* (2006.01)

(56) References Cited

U.S. PATENT DOCUMENTS

| | | |
|---|---|---|
| 2006/0230710 A1 | 10/2006 | Ishiwatari et al. |
| 2006/0271237 A1 | 11/2006 | Kim |
| 2007/0000805 A1 | 1/2007 | Van Den Brink |
| 2007/0265880 A1* | 11/2007 | Bartfeld et al. .................. 705/2 |
| 2008/0149657 A1* | 6/2008 | Kim .................................. 221/2 |
| 2009/0134181 A1* | 5/2009 | Wachman et al. ................ 221/8 |
| 2012/0216485 A1 | 8/2012 | Amano et al. |
| 2013/0197693 A1* | 8/2013 | Kamen et al. ................ 700/244 |

FOREIGN PATENT DOCUMENTS

| | | |
|---|---|---|
| JP | 2012-000440 A | 1/2012 |
| KR | 10-0650285 B1 | 11/2006 |
| KR | 10-2007-0018763 A | 2/2007 |
| KR | 10-0852493 | 8/2008 |
| KR | 10-0911061 | 8/2009 |
| KR | 10-2012-0104522 A | 9/2012 |
| WO | WO2009-061095 | 5/2009 |

* cited by examiner

MEDICATION DISPENSING APPARATUS FOR PREVENTING MEDICATION DISPENSING ERROR

CROSS-REFERENCE TO RELATED APPLICATION

This application claims priority from Korean Patent Application Nos. 10-2013-0017092 and 10-2013-0017094, filed on Feb. 18, 2013, in the Korean Intellectual Property Office, the entire disclosures of which are incorporated herein by references for all purposes.

BACKGROUND

1. Field

The following description relates to a medication dispensing apparatus, and more particularly, to a medication dispensing apparatus capable of preventing errors that may occur in medication dispensing process according to prescriptions.

2. Description of the Related Art

FIG. 1 is a diagram schematically illustrating an existing medication dispensing apparatus, and FIG. 2 is a perspective view illustrating a medication cabinet of FIG. 1.

A medication dispensing apparatus as shown in FIG. 1 that automatically creates unit-dose packages of medications in forms of pills, tablets, capsules, etc. is well known. The medication dispensing apparatus may include a medication cabinet 10 that contain pills categorized by type, and a packaging unit 20 that is disposed below the medication cabinet 10 and packages the medications provided from the medication cabinet 10. The medication cabinet 10 may include a cabinet body 11 and containers 12, as shown in FIG. 2. The cabinet body 11 has an inner space with at least one open side. For example, the cabinet body 11 may be a hollow box with one open side. The containers 12 may have a structure that allows a plurality of cartridges 13 to be mounted therein, and the cartridges 13 may be enabled to be withdrawn along with the containers 12 from the cabinet body 11. The cartridge 13 may include a cartridge case 13a and a cartridge base 13b attached to a lower part of the cartridge case 13a. The cartridge base 13a may store one type from among different types of pills. The cartridge base 13b may be controlled to discharge pills from the cartridge case 13a in response to a prescription signal.

Pills discharged from the cartridges 13 are conveyed through a transfer passage and dropped to corresponding intermediate shutters 30 where the pills are temporarily contained, or if no intermediate shutters 30 exist, the pills may be collected directly in a hopper 40. Korean Publication Registration No. 10-0911061 discloses the transfer passage. The intermediate shutters 30, if they exist, may each discharge the contained pills by opening one side. Accordingly, the pills are dropped from the intermediate shutters 30 and collected in the hopper 40. The pills accumulated in the hopper 40 are withdrawn to a packaging unit 20 positioned below the hopper 40, and the packaging unit 20 creates unit-dose packages. In this case, the packaging unit 20 may be configured in various ways. For example, the packaging unit 20 may include a conveyor to transport package paper, a sealing device to seal the package paper, and a printer to print on the package paper various information. Thus, the packaging unit 20 can automatically make unit-dose packages of pills.

In this example, the pills to be dispensed may fail to be discharged from the cartridges 13 due to a malfunction of the cartridges 13 or a system error, which leads to erroneous dispensing of medication. Therefore, to prevent such errors, an optical sensor 50 may be provided to an outlet 13b-1 of the cartridge base 13b, as shown in FIG. 3. This sensor 50 may monitor the discharge of pills, thereby making it possible to check whether the pills are discharged or not. However, there may be a case where the pills are all discharged from the cartridges 13, but not be accumulated in the hopper 40. For example, some pills dropped from the cartridges 13 may fail to reach the hopper 40 due to an unexpected condition of the transfer passage. Moreover, the optical sensor 50 only monitors whether the pills pass through the outlet 13b-1 of the cartridge 13, and hence even when powder flows through the outlet 13b-1, the optical sensor 50 may misidentify the powder residue as pills being discharged. Further, if the cartridge case 13a contains a different type of pill, which is not designated to the cartridge 13, the optical sensor 50 is not able to detect whether the wrong pills are discharged. Hence, there is still a possibility of making a medication dispensing error.

PRIOR ART REFERENCE

Patent Documents

Korean Patent Registration No. 10-0852493
Korean Patent Registration No. 10-0911061

SUMMARY

The following description relates to a medication dispensing apparatus capable of ensuring medication dispensing in accordance with a prescription.

In one general aspect, there is provided a medication dispensing apparatus for preventing a medication dispensing error, including: a communication unit configured to communicate with a manager server; a medication collecting unit configured to gather capsules or tablets for one dose that are discharged from cartridges; a medication image acquiring unit configured to acquire an image of the capsules or tablets contained in the medication collecting unit; and a control unit configured to comprise a dispensing information delivery unit to transmit to the manager server the medication information acquired by the medication image acquiring unit, and a dispensing control unit to continue a medication dispensing process or control capsules or tablets to be re-dispensed according to a user's dispensing control instruction received from the manager server.

The control unit may further include a medication image analyzing unit to analyze the acquired medication image, and a medication dispensing error determining unit to determine an occurrence of a medication dispensing error based on an analysis result from the image analyzing unit, and the dispensing information delivery unit may transmit to the manager server a determination made by the medication dispensing error detection unit.

The medication image analyzing unit may analyze at least one factor of the pills' numbers, shapes, colors and sizes within the acquired medication image.

The medication dispensing apparatus may further include a classifier configured to classify the medications from the medication collection unit to be either in a recovery area or in a packaging area.

The medication dispensing apparatus may further include a recovery marking unit configured to mark a package of capsules or tablets which are discharged from the medication collecting unit and are subject to recovery.

The recovery marking unit may be a punch unit.

In another general aspect, there is provided a medication dispensing apparatus for preventing a medication dispensing error, including: a medication collecting unit configured to contain capsules or tablets for one dose which are discharged from cartridges and to discharge the contained capsules or tablets to a packaging unit; a medication image acquiring unit configured to acquire an image of the capsules or tablets contained in the medication collecting unit; and a control unit configured to comprise a medication image analyzing unit to analyze the image acquired by the medication image acquiring unit, a medication dispensing error determining unit to determine an occurrence of a medication dispensing error by comparing prescription information and an analysis result from the medication image analyzing unit and a dispensing control unit to continue a medication dispensing process or control capsules or tablets to be re-dispensed according to a determination made by the medication dispensing error detection unit.

The medication image analyzing unit may analyze at least one factor of the pills' numbers, shapes, colors, and sizes within the acquired medication image.

The medication dispensing apparatus may further include a weight measuring unit configured to measure a total weight of the capsules or tablets contained in the medication collection unit, wherein the medication dispensing error detection unit takes into consideration the measured weight to determine the occurrence of medication dispensing error.

The medication dispensing apparatus may further include a classifier configured to classify the medications from the medication collection unit to be either in a recovery area or in a packaging area.

The medication dispensing apparatus may further include a recovery marking unit configured to mark a package of capsules or tablets which are discharged from the medication collection unit and are subject to recovery.

The recovery marking unit may be a punch unit.

In another general aspect, there is provided a medication dispensing apparatus for preventing a medication dispensing error, including: a medication collecting unit configured to contain capsules or tablets for one dose which are discharged from cartridges and to discharge the contained capsules or tablets to a packaging unit; a medication image acquiring unit configured to acquire an image of the capsules or tablets contained in the medication collection unit; and a control unit configured to comprise a medication image analyzing unit to analyze the image acquired by the medication image acquiring unit, a medication dispensing error detection unit to determine an occurrence of a medication dispensing error based on an analysis result from the medication image analyzing unit, a medication dispensing information providing unit to provide to a user information on prescribed medication, the medication image acquired by the medication image acquiring unit and a determination made by the medication dispensing error detection unit, and a dispensing control unit to continue a medication dispensing process or control capsules or tablets to be re-dispensed according to a user's input or the determination made by the medication dispensing error detection unit.

The medication dispensing apparatus may further include a display unit, wherein the medication dispensing information providing unit outputs to the display unit the medication image acquired by the medication image acquiring unit and the determination made by the medication dispensing error detection unit.

The dispensing control unit may continue the medication dispensing process, or control capsules or tablets to be re-dispensed, according to a user's input in user mode, or according to the determination made by the medication dispensing error detection unit in automatic mode.

The medication image analyzing unit may analyze at least one factor of the pills' numbers, shapes, colors, and/or sizes within the acquired medication image.

The medication dispensing apparatus may further include a weight measuring unit configured to measure a total weight of the capsules or tablets contained in the medication collecting unit, wherein the medication dispensing error detection unit takes into consideration the measured weight to determine the occurrence of medication dispensing error.

The medication dispensing apparatus may further include a classifier configured to classify the medications from the medication collecting unit to be either in a recovery area or in a packaging area.

The medication dispensing apparatus may further include a recovery marking unit configured to mark a package of capsules or tablets which are discharged from the medication collecting unit and are subject to recovery.

The recovery marking unit may be a punch unit.

Other features and aspects will be apparent from the following detailed description, the drawings, and the claims.

Figure 1:
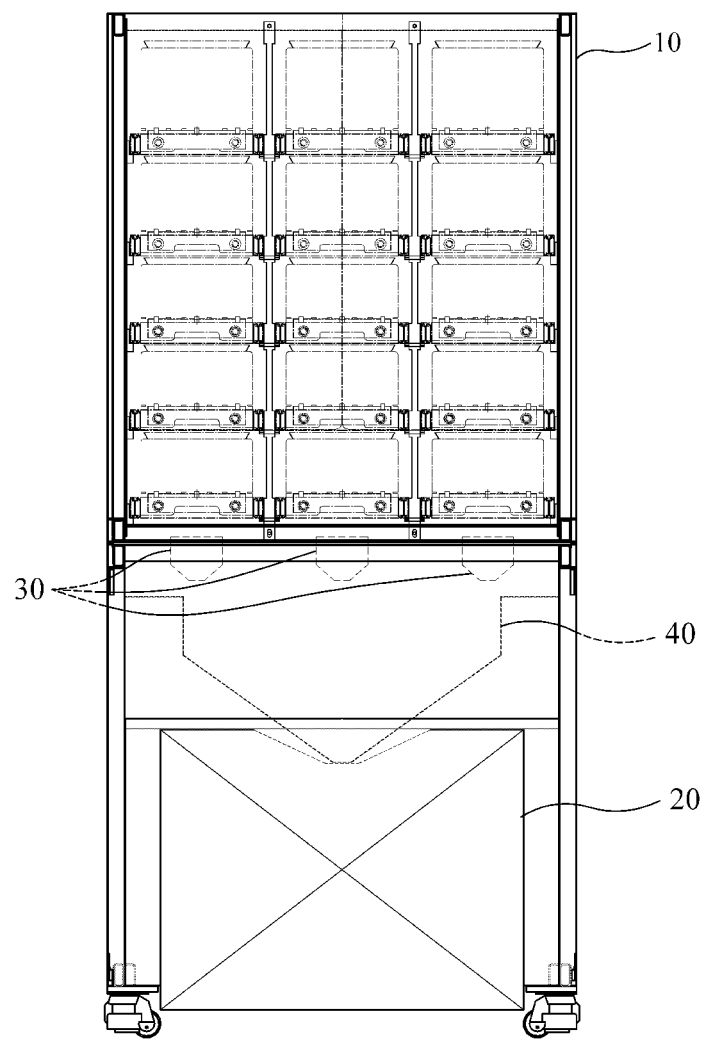
FIG. 1 is a diagram schematically illustrating a medication dispensing apparatus according to a related art.
Figure 2:
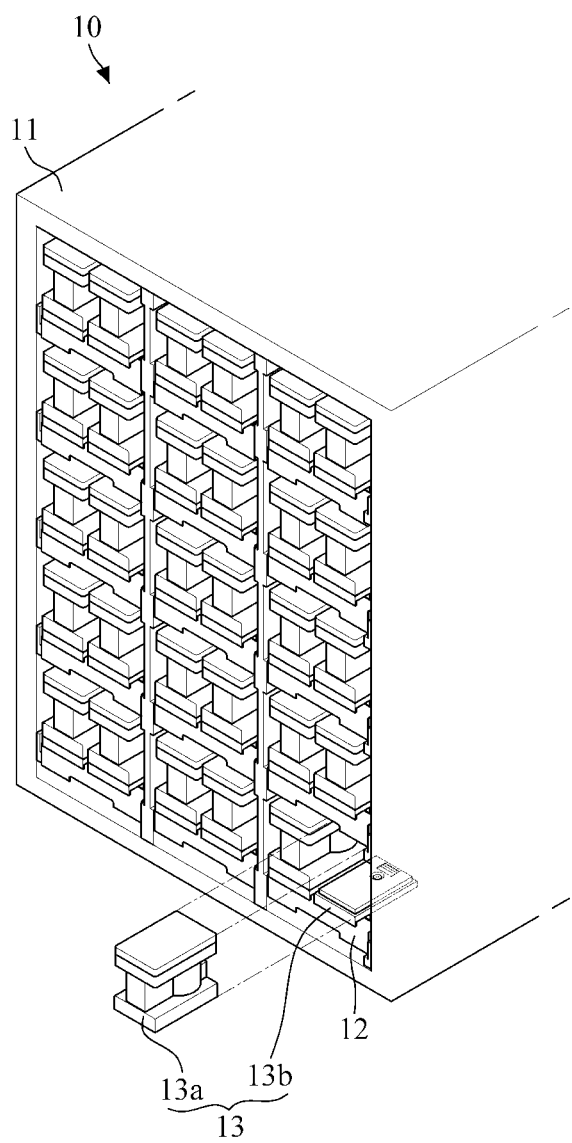
FIG. 2 is a perspective view illustrating a medication cabinet of FIG. 1.
Figure 3:
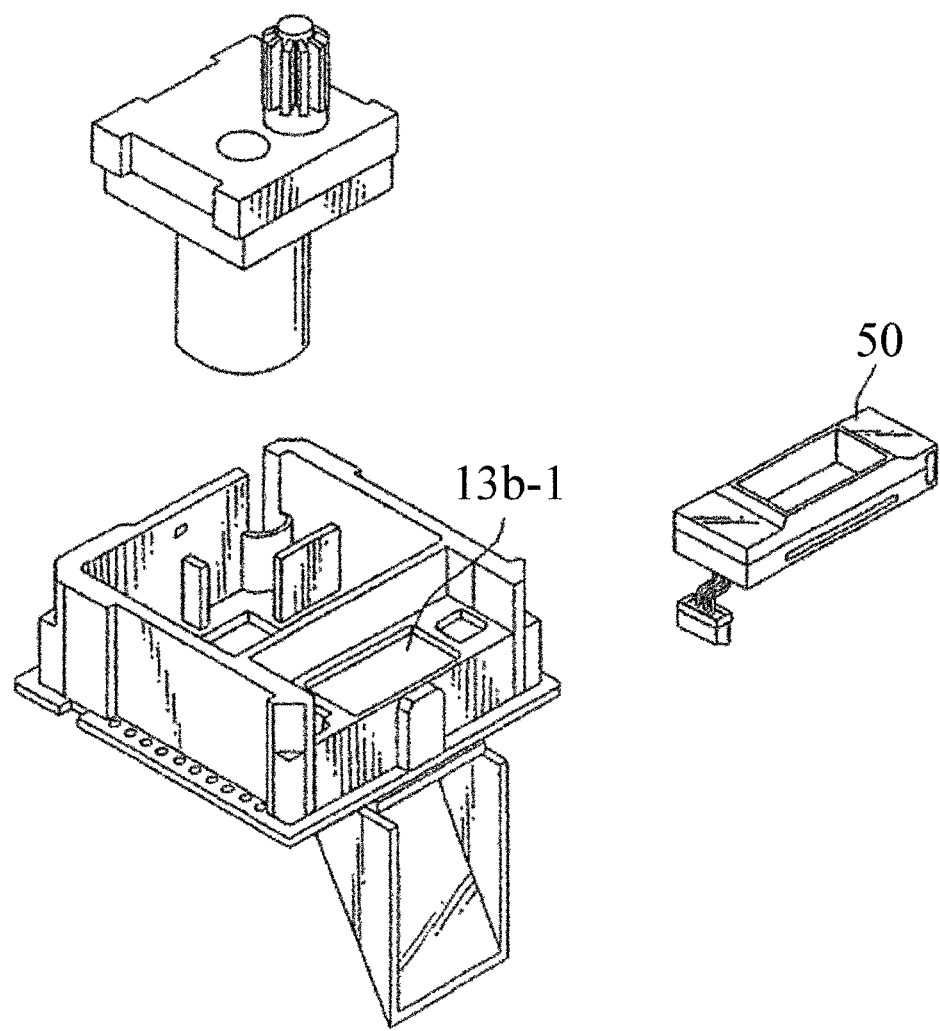
FIG. 3 is a perspective view illustrating a cartridge base according to a related art.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 4:
FIG. 4 is a block diagram illustrating a dispensing inspection system according to an exemplary embodiment of the present invention.

FIG. 4 is a block diagram illustrating a dispensing inspection system according to an exemplary embodiment of the present invention.

Referring to FIG. 4, the dispensing inspection system may include a medication dispensing apparatus 100 and a manager server 200, and additionally a communication terminal 300. Generally, the medication dispensing apparatus 100 may discharge capsules or tablets from different cartridges according to prescription data, and automatically create unit-dose packages of medication. In addition, the medication dispensing apparatus 100 may photograph the capsules or tablets in one unit-dose package, and transmit the photographed image of the medication to the manager server 200. The manager server 200, which is capable of working in conjunction with and controlling the medication dispensing apparatus 100, may transfer the prescription data to the medication dispensing apparatus 100. In addition, the manager server 200 may receive the medication image from the medication dispensing apparatus 100 and display the received image on a display screen, and at this time, may further display information on prescribed medication for comparison purposes. Here, the information on prescription medication refers to information about capsules or tablets in one unit-dose package according to the prescription data, and may include sample images, numbers and names of the capsules or tablets. Accordingly, a user may be able to check a medication dispensing error based on the medication image, or by comparing the mediation image and the information on prescribed medication. Here, the user may be a pharmacist, who manages the medication dispensing process. If no medication dispensing error is found, the user may issue an instruction to proceed with the dispensing process. Otherwise, the user may instruct to re-dispense the medication. The manager server 200 may transfer a user's dispensing control instruction to the medication dispensing apparatus 100, and in response to the dispensing control instruction, the medication dispensing apparatus 100 may continue the dispensing process or re-dispense the medication.

In addition, the user may be able to remotely check an error in medication dispensing by means of the communication terminal 300. The communication terminal 300 may be a desktop computer, or a mobile terminal. The communication terminal 300 may have an application installed therein to allow the user to check a medication dispensing error. By running the application, the communication terminal 300 may remotely access the manager server 200: it receives the medication image and information on prescribed medication from the manager server 200, and outputs the received image and information to a display screen. Accordingly, the user is able to visibly check the medication dispensing error while watching the display screen of the communication terminal 300. In response to a dispensing control instruction input by the user in accordance with the examined results, the communication terminal 300 may deliver the received dispensing control instruction to the manager server 200. Then, the manager server 200 may deliver the received dispensing control instruction to the medication dispensing apparatus 100.

Figure 5:
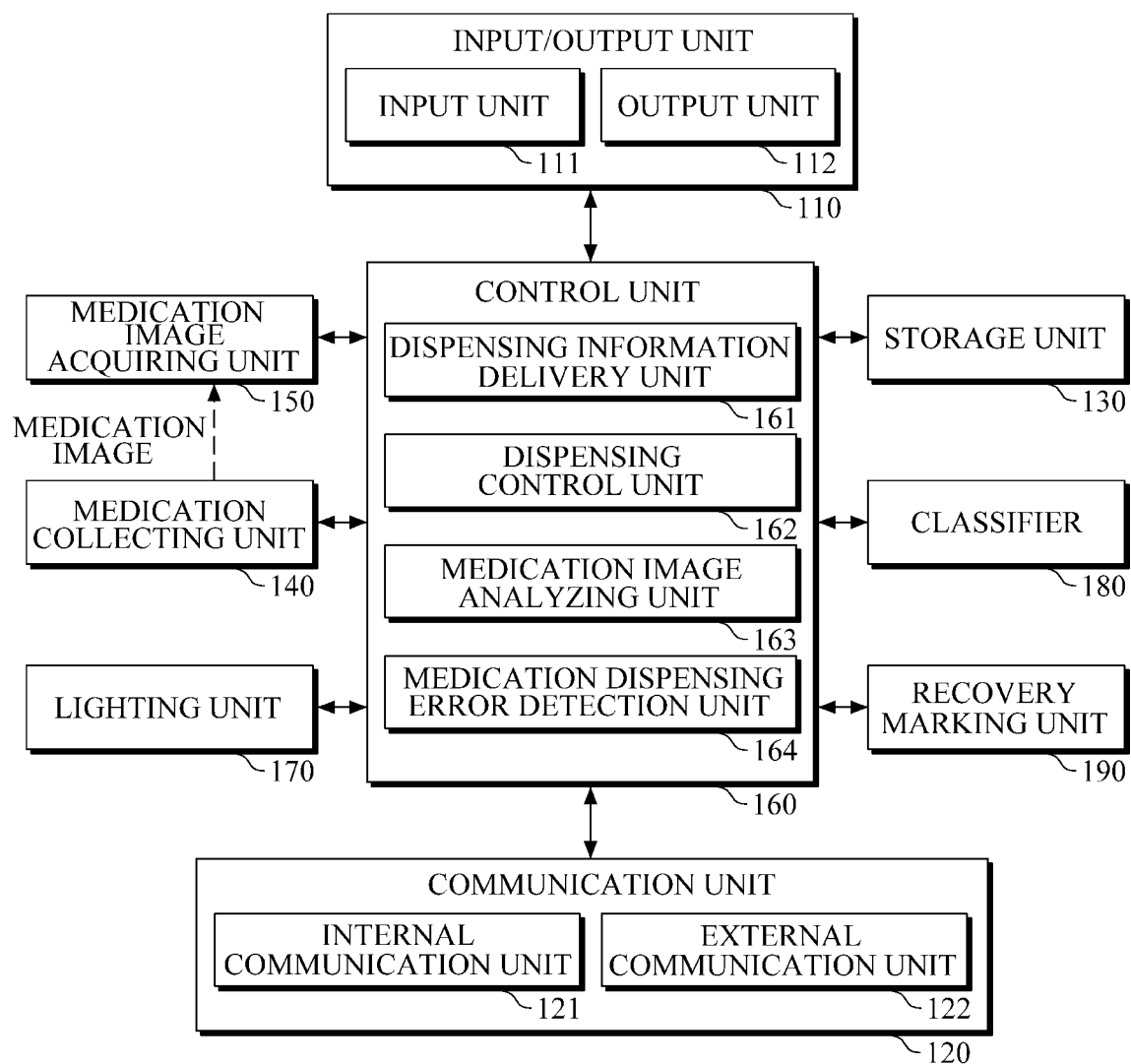
FIG. 5 is a block diagram illustrating a medication dispensing apparatus according to an exemplary embodiment of the present invention.

FIG. 5 is a block diagram illustrating a medication dispensing apparatus according to an exemplary embodiment of the present invention.

Referring to FIG. 5, a medication dispensing apparatus 100 may include an input/output unit 110, a communication unit 120, a storage unit 130, a medication collecting unit 140, a medication image acquiring unit 150, and a control unit 160. The input/output unit 110 may include an input unit 111 and a display unit 112. The input unit 111 may include a number of buttons, a touch pad, or the like, to receive touch inputs. The display unit 112 may be a liquid crystal display (LCD), light emitting diode (LED) display, an organic light emitting diode (OLED) display, or the like. The communication unit 120 may include an internal communication unit 121, and an external communication unit 122. The internal communication unit 121 is configured to allow communications between units, such as cartridges, which are within the medication dispensing apparatus, and may follow wired-communication standards in an effort to ensure communication reliability, and as a serial communication, half-duplex communication may be established. The external communication unit 122 may be configured to enable communication with the manager server 200, and may follow wired or wireless communication standards. The storage unit 130 may include non-volatile memory, and store control programs and data required for dispensing and packaging the medication.

The medication collecting unit 140 may gather capsules or tablets for one unit-dose packaging, which are discharged from the cartridges according to the prescription data, and then release them. In one example, the medication collecting unit 140 may be a hopper that collects all capsules or tablets, and discharges them to a packaging unit. The medication collecting unit 140 may include an opening means (i.e., a shutter) that opens or closes the medication collecting unit 140, thereby controlling the discharge of the capsules or tablets. The medication image acquiring unit 150 may acquire an image (hereinafter referred to as a "medication image") of the capsules or tablets collected in the medication collecting unit 140, and may include a camera to capture an image of an area where collection of the capsules or tablets occur. Furthermore, to improve the resolution of the captured image, the medication image acquiring unit 150 may further include a lighting unit 170 to illuminate an area to be photographed. The lighting unit 170 may use various light sources, such as visible light, infrared light, ultraviolet light, laser light, X-ray light, and the like.

The control unit 160 may be a control module that includes one or more image processors, and a central processing unit. The control unit 160 may control the discharge of the capsules or tablets from the cartridges according to the prescription data received from the manager server 200. The control unit 160 may include a dispensing information delivery unit 161, and a dispensing control unit 162, to prevent medication dispensing errors. The dispensing information delivery unit 161 may transmit to the manager server 200 the medication image acquired by the medication image acquiring unit 150 via the external communication unit. Then, the dispensing control unit 162 may dictate the continuation of the dispensing process, or the re-dispensing of medication. To continue the dispensing process, the dispensing control unit 162 may discharge the capsules or tablets collected in the medication collecting unit 140 to the packaging unit. Then, the packaging unit packages the capsules or tablets. To re-dispense the medication, the dispensing control unit 162 may recover the capsules or tablets contained in the medication collecting unit 140, and direct the capsules or tablets to be packed in unit-dose packages.

Figure 6:
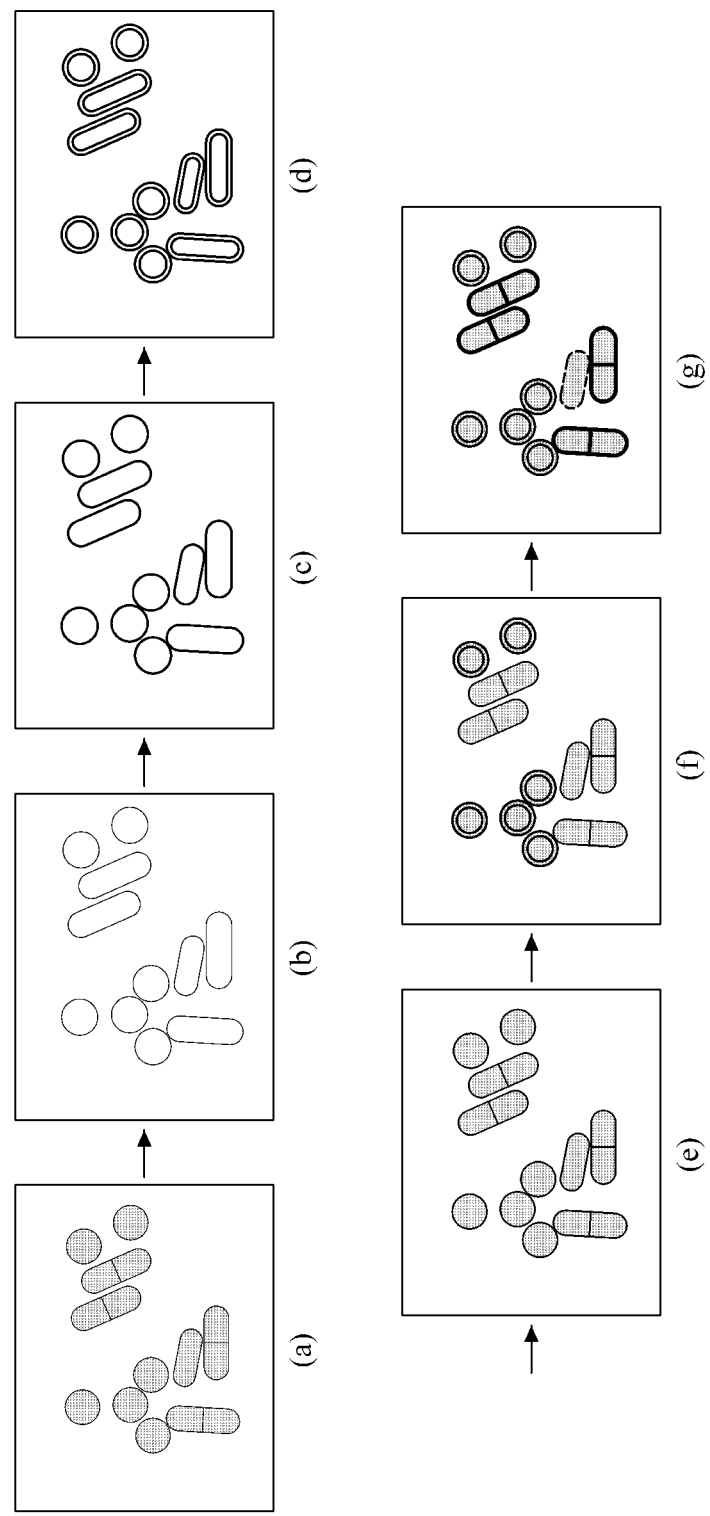
FIG. 6 is a diagram illustrating an example of a display screen of a shape-based image analysis according to an exemplary embodiment of the present invention.

The control unit 160 may further include a medication image analyzing unit 163 and a medication dispensing error detection unit 164. The medication image analyzing unit 163 may analyze the medication image acquired by the medication image acquiring unit 150. In one example, the medication image analyzing unit 163 may analyze, from the medication image, at least one of characteristics, such as the total number of the pills, the number of each type of pill, and shapes, colors, and sizes of the pills. The medication image analyzing unit 163 may analyze whether there is a defective pill, such as a cracked pill, or whether there is a foreign substance on the medication. For the image analysis, the medication image analyzing unit 163 may perform a shape-based image analysis, which is described below with reference to FIG. 6.

(a) acquire a photographed image of the capsules or tablets to be dispensed
(b) enlarge the acquired image (apply Scale_image)
(c) extract predicted medication (capsule or tablet) regions (threshold)
(d) perform "erosion" on the extracted medication regions to distinguish overlapping capsules or tablets from the image, apply an "opening" operation to reconstruct the shapes of the overlapping capsules or tablets, perform a "connection" operation, and perform "dilation" to achieve return to actual medication region
(e) delete remaining regions, other than the medications, from the image
(f) identify the capsules or tablets (shapes and colors)
(g) extract the medication regions, form an arbitrary oval encircling each of the extracted medication regions, and compare the longest axis and the shortest axis of each oval to determine the corresponding medication as one of a circle, an oval, or a smaller oval The dispensing error detection unit 164 may determine the medication dispensing error based on the image analysis result of the medication image analyzing unit 163. In one example, the dispensing error detection unit 164 may determine the medication dispensing error by comparing the analysis result of the medication image analyzing unit 163 with the information on a prescribed medication, the determination of which may be made within an appropriate error range. In addition, the information on prescribed medication may be delivered from the manager server 200, along with the prescription data. Alternatively, detailed information of all medications contained in the cartridges may be stored in the storage unit 130. The medication dispensing error determining unit 164 may search the storage unit 130 to check the information on prescribed medication related to the prescription data. The medication dispensing error detection unit 164 may compare the information on the prescribed medication and the analysis result. If the compared result indicates that they match, the medication dispensing error detection unit 164 may determine that the dispensing has been made correctly, or conversely, may determine that there is an error in medication dispensing. In addition, the dispensing information delivery unit 161 may transmit to the manager server 200 the determination data created by the medication dispensing error detection unit 164, along with the medication image.

Figure 7:
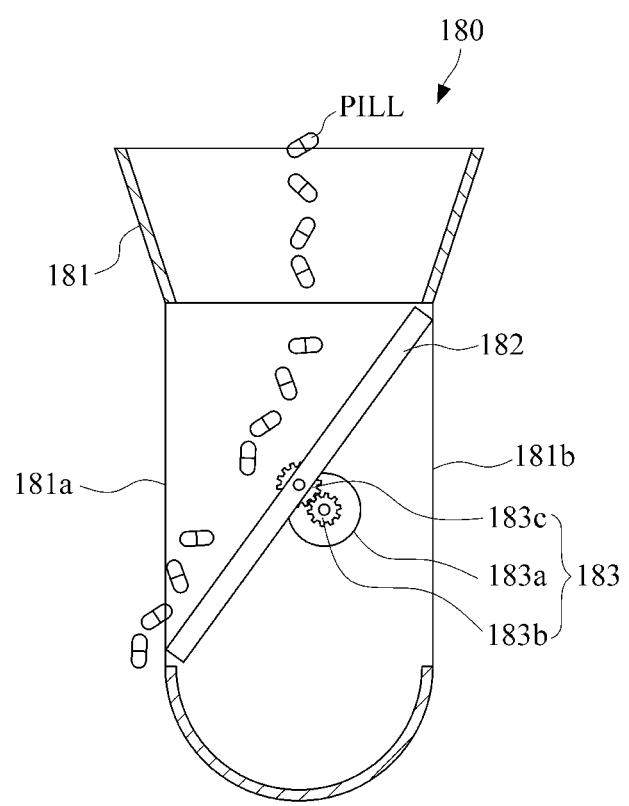
FIG. 7 is a diagram illustrating a classifier according to an exemplary embodiment of the present invention.
Figure 8:
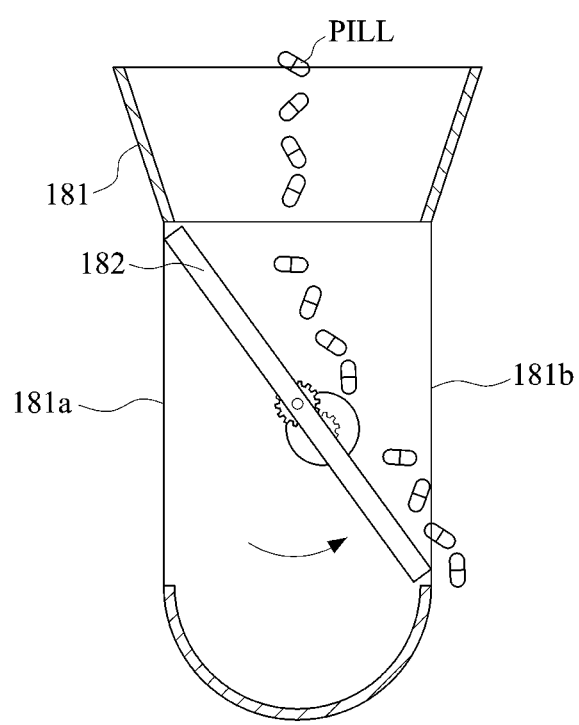
FIG. 8 is a diagram showing how the classifier of FIG. 7 operates.

To recover the capsules or tablets in the event of detecting the medication dispensing error, the medication dispensing apparatus 100 may further include a classifier 180 or a recovery marking unit 190. As shown in FIGS. 7 and 8, the classifier 180 is disposed below the hopper 140, and may include a classification container 181 which has an open top and a first opening 181a and a second opening 181b on each side, and a classification plate 182 to selectively open the first opening 181a and the second opening 181b according to a rotation movement of a classification plate driving unit 183. The classification container 181 may receive the capsules or tablets discharged from the hopper 140 through the open top. The first opening 181a may allow the discharge of the pills or tablets that are determined as being correctly dispensed, so that they can be packaged. The second opening 181b may allow the recovery of the pills or tablets that are determined as being erroneously dispensed. The classification plate 182 may be tilted at an angle to allow the first opening 181a to fully open, so that the capsules and tablets can be smoothly led to the first opening 181a, as shown in FIG. 7. In addition, the classification plate 182 may be tilted at an angle to allow the second opening 181b to fully open, so that the erroneously dispensed capsules or tablets can be smoothly led to the second opening 181b, as shown in FIG. 8.

The classification plate driving unit 183 may be controlled by the control unit 160. The control unit 160 may control the classification plate driving unit 183 to selectively open the first opening 181a and second opening 181b according to the determination on the occurrence of the medication dispensing error. For example, the classification plate driving unit 183 may include a rotation motor 183a, a driving gear 183b coupled to a rotational axis of the rotation motor 183a, and a slave gear engaged with the driving gear 183b and coupled to the classification plate 182. The classification plate 182 is enabled to rotate by the rotation force transmitted from the rotation motor 183a via the driving gear 183b and the slave gear 183c. However, aspects need not be limited thereto, such that the classification plate driving unit 183 may be configured in various ways as long as it can rotate the classification plate 182.

Figure 9:
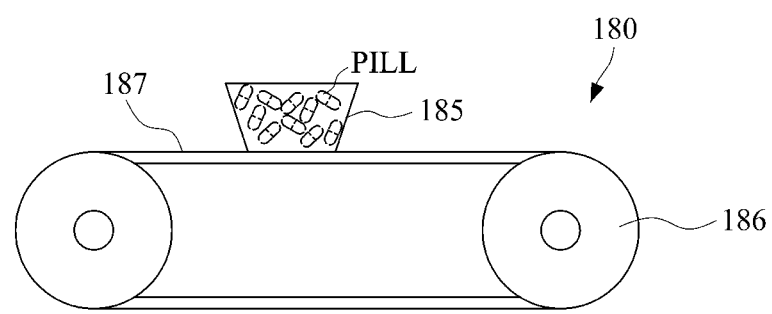
FIG. 9 is a diagram illustrating a classifier according to another exemplary embodiment of the present invention.
Figure 10:
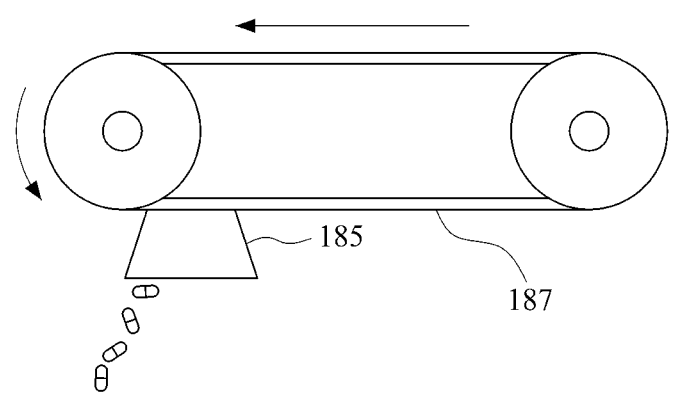
FIGS. 10 and 11 are diagrams showing how the classifier of FIG. 9 operates.
Figure 11:
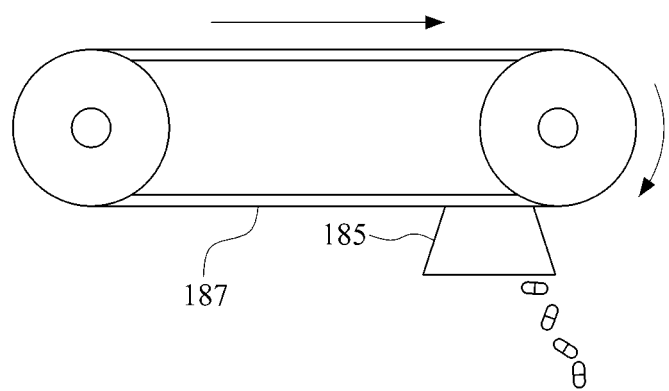

In another example, as shown in FIGS. 9 to 11, the classifier 180 may include a classification container 185 with an open top and a conveyor 186 through which the classification container 185 is transported. The capsules or tablets discharged from the hopper 140 may be provided to the classification container 185 through the open top. The classification container 185 has a bottom affixed to a belt 187 of the conveyor 186, which enables it to be conveyed by the rotation movement of the belt 187. For example, a lower left-hand side area of the conveyor 186 may be designated as a packaging area for packaging the normally dispensed capsules or tablets, and a lower right-hand side area may be designated as a recovery area for recovering the erroneous capsules or tablets. In this case, if correctly dispensed capsules or tablets are provided to the classification container 185, the belt 187 rotates in a counterclockwise direction as shown in FIG. 10, so that the classification container 185 can be conveyed to the left side and turned over, thereby dropping the capsules or tablets from the container 185 to the packaging area. If erroneous capsules or tablets are provided to the classification container 185, the belt 187 rotates in a clockwise direction as shown in FIG. 11, so that the classification container 185 can be conveyed to the right side and turned over, thereby dropping the capsules or tablets within the container 185 to the recovery area. The conveyor 186 may be controlled by the control unit 186. The control unit 160 may transport the classification container 185 selectively to the packaging area or the recovery area by controlling the rotation direction of the belt 187 in accordance with the determination of the occurrence of the medication dispensing error. However, aspects of the invention are not limited thereto such that the classifier 180 may be configured in various ways as long as it can perform the aforementioned functions.

The recovery marking unit 190 will now be described in detail. The recovery marking unit 190 may mark a package of capsules or tablets to be re-collected or recovered. In one example, the recovery marking unit 190 may be a punching unit to make one or more small holes on the package of medication. The punching unit may be disposed at an appropriate position on an upper portion of the conveyor 186, such that it can punch one or more holes in the package of capsules or tablets, which is transported over the conveyor 186. In response to a re-dispensing instruction transmitted from the manager server 200, the dispensing control unit 162 may discharge the capsules or tablets from the medication collection unit 140 in the same manner as when the dispensing process is normally performed, such that the pills can be packaged by the packaging unit. However, the capsules or tablets in the existing packages, which have been determined as being erroneous are subject to recovery, and thus the dispensing control unit 162 may control the recovery marking unit 192 to mark the packages of the capsules or tablets to be recovered.

Accordingly, it is possible to easily identify and remove the packages containing the pills subject to recovery.

Figure 12:
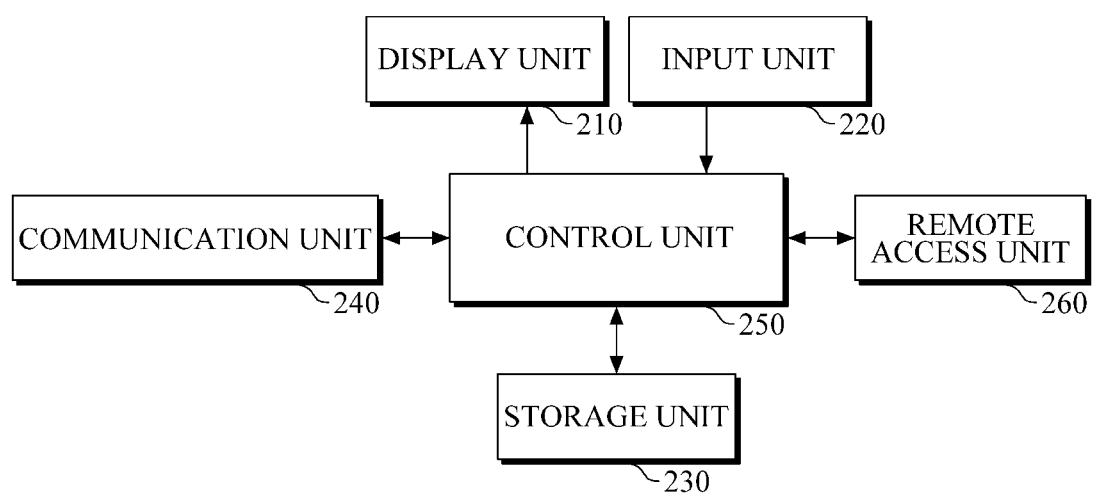
FIG. 12 is a block diagram illustrating a manager server according to an exemplary embodiment of the present invention.

FIG. 12 is a block diagram illustrating a manager server according to an exemplary embodiment of the present invention.

Referring to FIG. 12, a manager server 200 may include a display unit 210, an input unit 220, a storage unit 230, a communication unit 240, and a control unit 250. The display unit 210 may be an LED display, a thin film transistor-liquid crystal display (TFT-LCD), etc. The input unit 220 may be an interface to allow touch inputs. In this case, the input unit 220 may be integrated with the display unit 210, thereby being implemented as a touch screen. The storage unit 230 may be of non-volatile memory, which may be used for a black-box function for monitoring medication dispensing process, which will be described later. The communication unit 240 allows a communication with the medication dispensing apparatus 100, and may conform to wired or wireless communication standards. The control unit 160 may be a control processing unit (CPU). The control unit 160 may receive a medication image from the medication dispensing apparatus 100 via the communication unit 240, and may further receive data related to determination of the occurrence of medication dispensing error.

Figure 13:
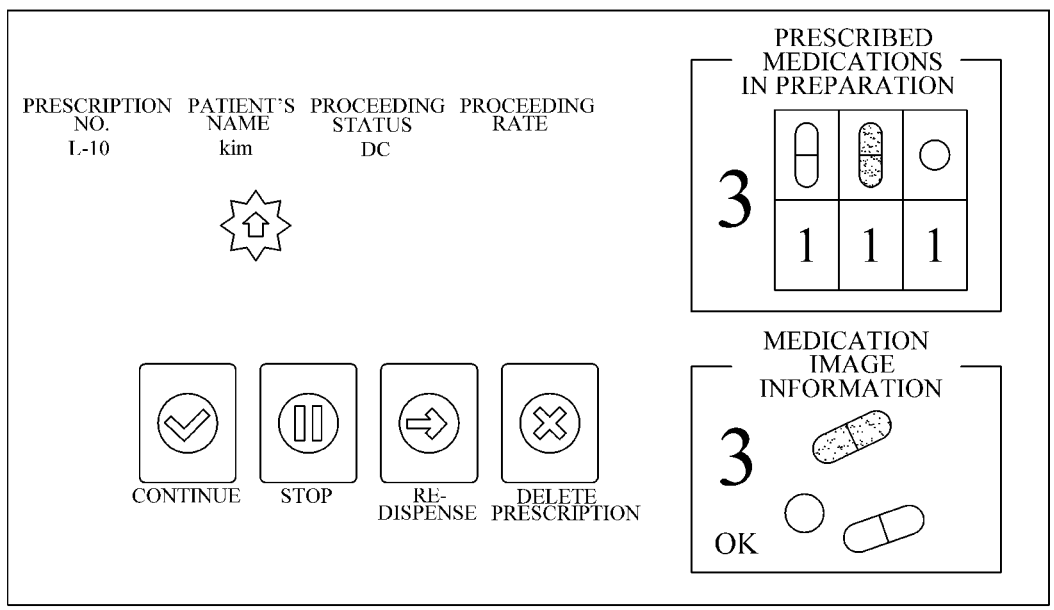
FIGS. 13 to 16 are diagrams illustrating examples of a UI screen according to an exemplary embodiment of the present invention.
Figure 14:
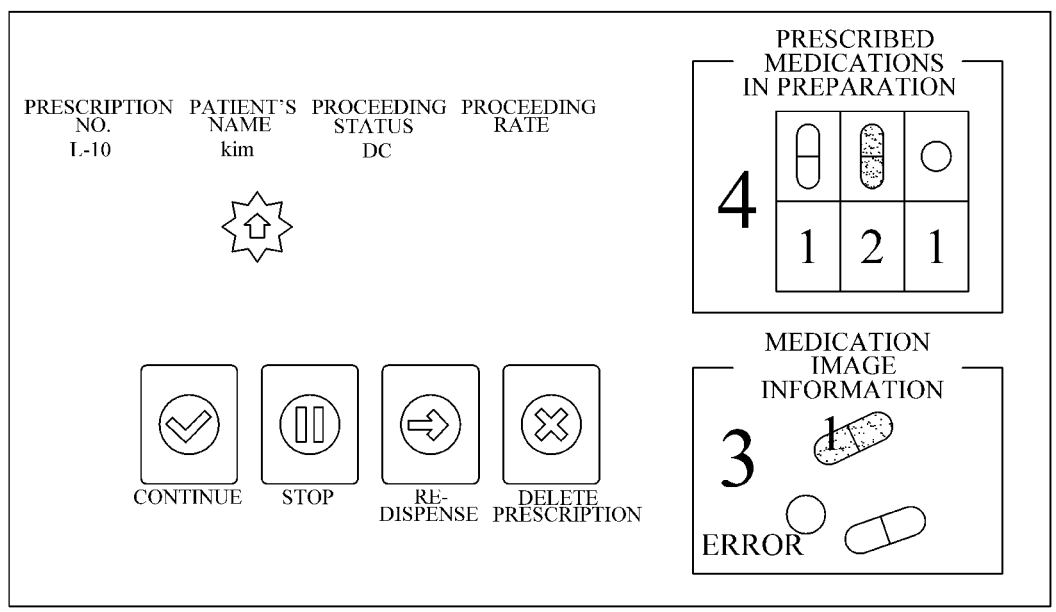

The control unit 250 may output the received medication image to the display unit 210. In addition, the control unit 250 may output information on prescribed medications to the display unit 210 in an effort to assist in a user's inspection of the dispensing process. The information on prescribed medications, which is displayed on the display unit 210, may include sample images of capsules or tablets, the total number of capsules and tablets, and the number of each type of pills. Further, in response to the data related to determination of the occurrence of medication dispensing error received from the medication dispensing apparatus 100, the control unit 250 may output the received data to the display unit 210. FIGS. 13 and 14 illustrate examples of a user interface (UI) screen that can be displayed in the above situations. FIG. 13 illustrates a normal UI when the medication dispensing is correctly performed, and FIG. 14 illustrates a UI when a medication dispensing error has been detected. Referring to FIG. 13, "PRESCRIBED MEDICATIONS IN PREPARATION" displayed on the top right side shows prescription information indicating that three different types, and a total of three pills (one for each type) are prescribed. In addition, medication image information at a lower right side may display both the medication image received from the medication dispensing apparatus 100 and the data related to determination of the occurrence of medication dispensing error, showing "OK" to indicate that there is no medication dispensing error. After checking the displayed information, the user may select the "CONTINUE" button to proceed with the dispensing process. In response to selecting the "CONTINUE" button, the control unit 250 may transmit a dispensing control instruction to the medication dispensing apparatus 100.

Referring to FIG. 14, "PRESCRIBED MEDICATIONS IN PREPARATION" displayed on the top right side indicates that three different types and a total of four pills are prescribed, which include two pills of the same type and two pills of different types. Medication image information displayed on the bottom right side shows that there are three types and a total of three pills (one for each type), and from this medication image information, it is determined that there is a medication dispensing error that the dispensed pills do not match the prescription. An erroneous item may be made more noticeable by using a different color, as shown in 14. Once the error is confirmed, the user may select the "STOP" button to terminate the dispensing process, or select the "RE-DISPENSE" button to re-perform the dispensing process. In response to selecting the "RE-DISPENSE" button, the control unit 250 may transmit a corresponding dispensing control instruction to the medication dispensing apparatus 100.

Figure 15:
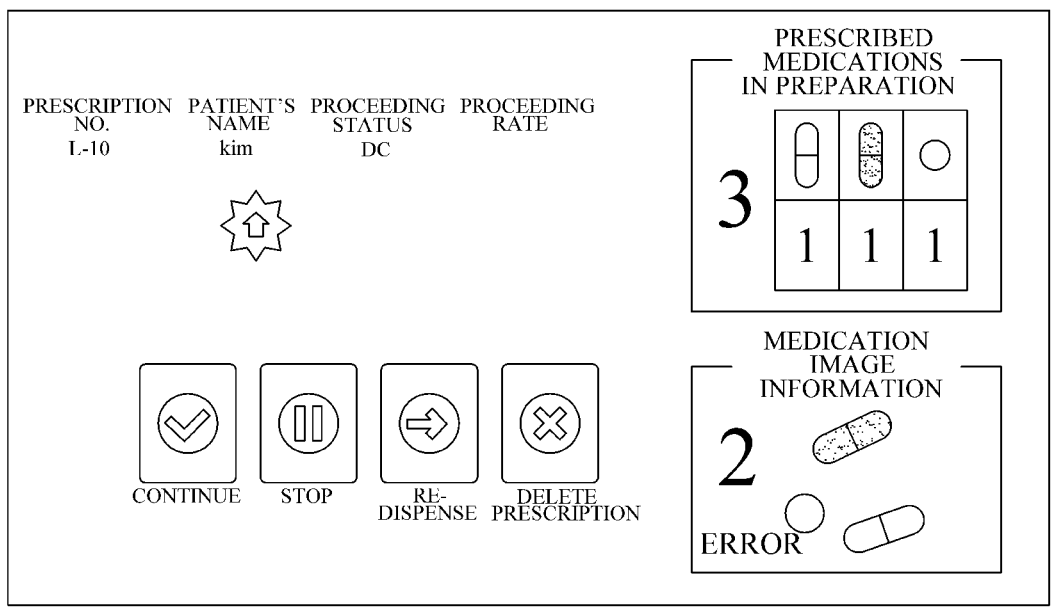
Figure 16:
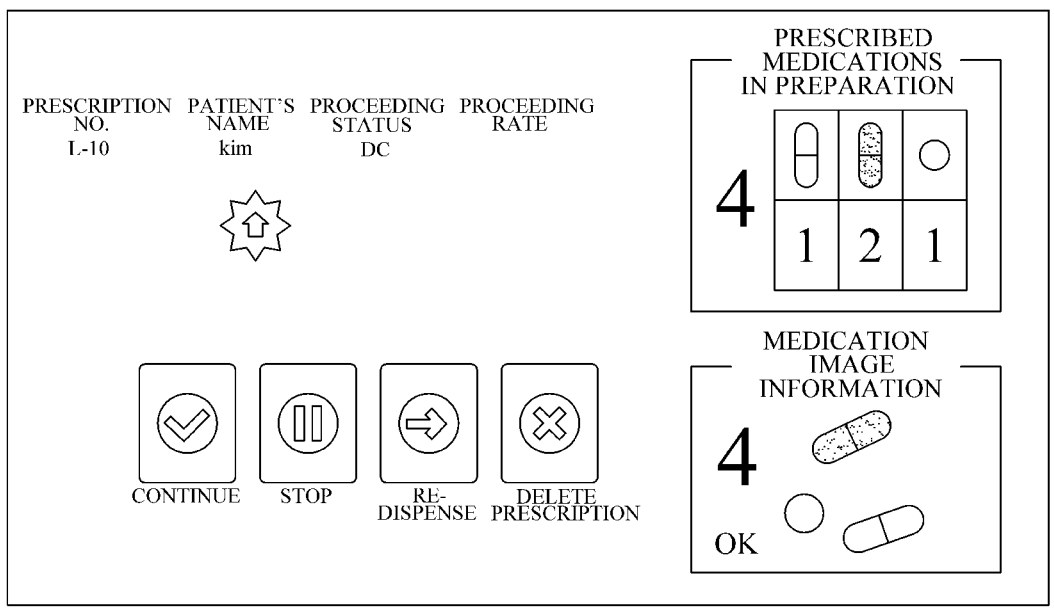

FIGS. 15 and 16 illustrate examples of a UI screen when there is an error in image analysis. FIG. 15 illustrates a UI screen when a medication dispensing error occurs due to the error in image analysis even when prescribed pills indicated by medication information of "PRESCRIBED MEDICATIONS IN PREPARATION" are identical to the dispensed pills indicated by medication image information. FIG. 16 illustrates a UI when the medication dispensing is performed correctly due to the error in image analysis even when prescribed pills indicated by medication information of "PRESCRIBED MEDICATIONS IN PREPARATION" do not match dispensed pills indicated by medication image information. In this case, the user may visually check and compare the pills in preparation for dispensing and the medication image information, and thereby confirm that the determination made on the occurrence of medication dispensing error is wrong. Thus, in a case shown in FIG. 15, the user may select the "CONTINUE" button, instead of "STOP", to enable the dispensing process to be continued. In a case shown in FIG. 16, the user may select "RE-DISPENSE" button to restart the medication dispensing.

In another aspect, the manager server 200 may further include a remote access unit 260. The remote access unit 260 may enable the manager server 200 to establish a channel with the communication terminal 300, which remotely accesses the manager server 200, to allow data transmission and reception through the channel. When the user runs a medication dispensing inspection application installed in the communication terminal 300, the communication terminal 300 attempts to access the manager server 200, and the remote access unit 260 authenticates the attempting communication terminal 300 to establish a channel with it. When the communication terminal 300 successfully gains the remote access to the manager server 200, the control unit 160 may transmit to the communication terminal 300 the medication image and the information on prescribed medication. Additionally, the control unit 160 may also transmit the data related to determination of the occurrence of medication dispensing error to the communication terminal 300. The communication terminal 300 may display on the display screen the received medication information, information on prescribed medication, and data related to determination. The user may verify whether the medication dispensing process has been performed normally while monitoring the UI screen of the communication terminal 300, and may issue a dispensing control instruction according to the verification result. The UI screen may be designed to be the same as or similar to those shown in FIGS. 13 to 16. The communication terminal 300 transmits the dispensing control instruction of the user to the manager server 200, and the manager server 200 transmits the received dispensing control instruction to the medication dispensing apparatus 100. Therefore, it is possible for the user to easily inspect the medication dispensing remotely.

Figure 17:
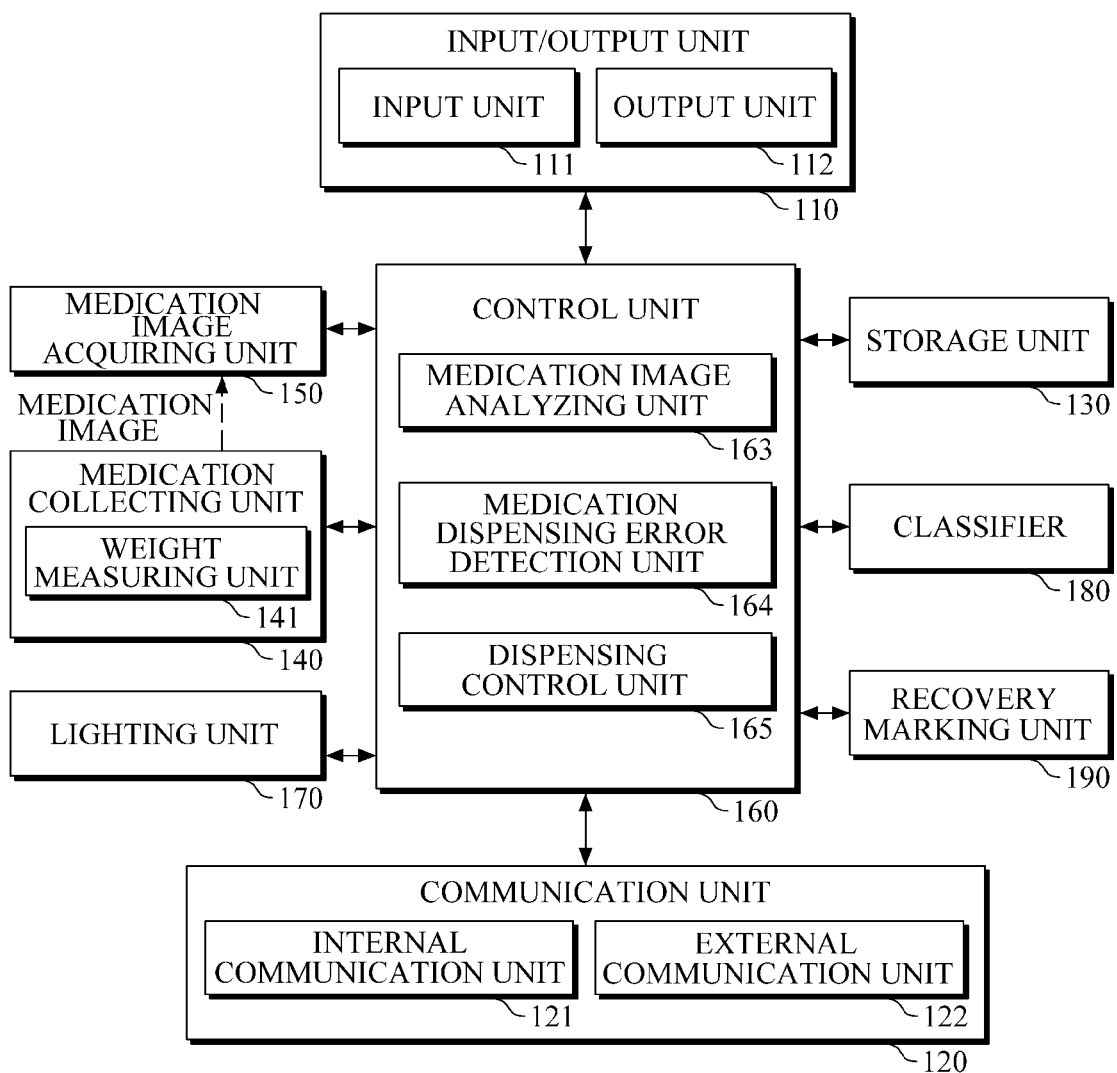
FIG. 17 is a block diagram illustrating a medication dispensing apparatus according to another exemplary embodiment of the present invention.

FIG. 17 is a block diagram illustrating a medication dispensing apparatus according to another exemplary embodiment of the present invention. Referring to FIG. 17, a medication dispensing apparatus has the same configuration as the medication dispensing apparatus shown in FIG. 5, except for the control unit 160. A control unit 160 shown in FIG. 17 includes a medication image analyzing unit 163, a medication dispensing error detection unit 164, and a dispensing control unit 165. The medication image analyzing unit 163 and the medication dispensing error detection unit 164 are the same as those illustrated in FIG. 5, and the dispensing control unit 165 is different from the dispensing control unit 162 of FIG. 5. In FIG. 17, the dispensing control unit 165 may control the medication dispensing process to be continued or the medication to be re-dispensed, according to the determination of the medication dispensing error detection unit 164. More specifically, the dispensing control unit 165 may allow the dispensing process to be continued if the analysis result of the medication image is identical with the information on prescribed medication. Otherwise, the dispensing control unit 165 may control the medication to be re-dispensed. In this example, the same methods as described above are applied for proceeding with the dispensing process and for re-dispensing the medication. In addition, the medication collecting unit 140 may further include a weight measuring unit 141. The weight measuring unit 141 may be an electronic scale to measure the total weight of the capsules or tablets contained in the medication collecting unit 140, located at a predetermined position below the hopper. The medication image analyzing unit 163 may further take into consideration the weight obtained from the weight measurement unit 141 when determining the occurrence of the medication dispensing error. In FIG. 17, the elements, other than the dispensing control unit 165, may be the same as the elements illustrated in FIG. 5, and thus the detailed descriptions thereof will not be reiterated.

Figure 18:
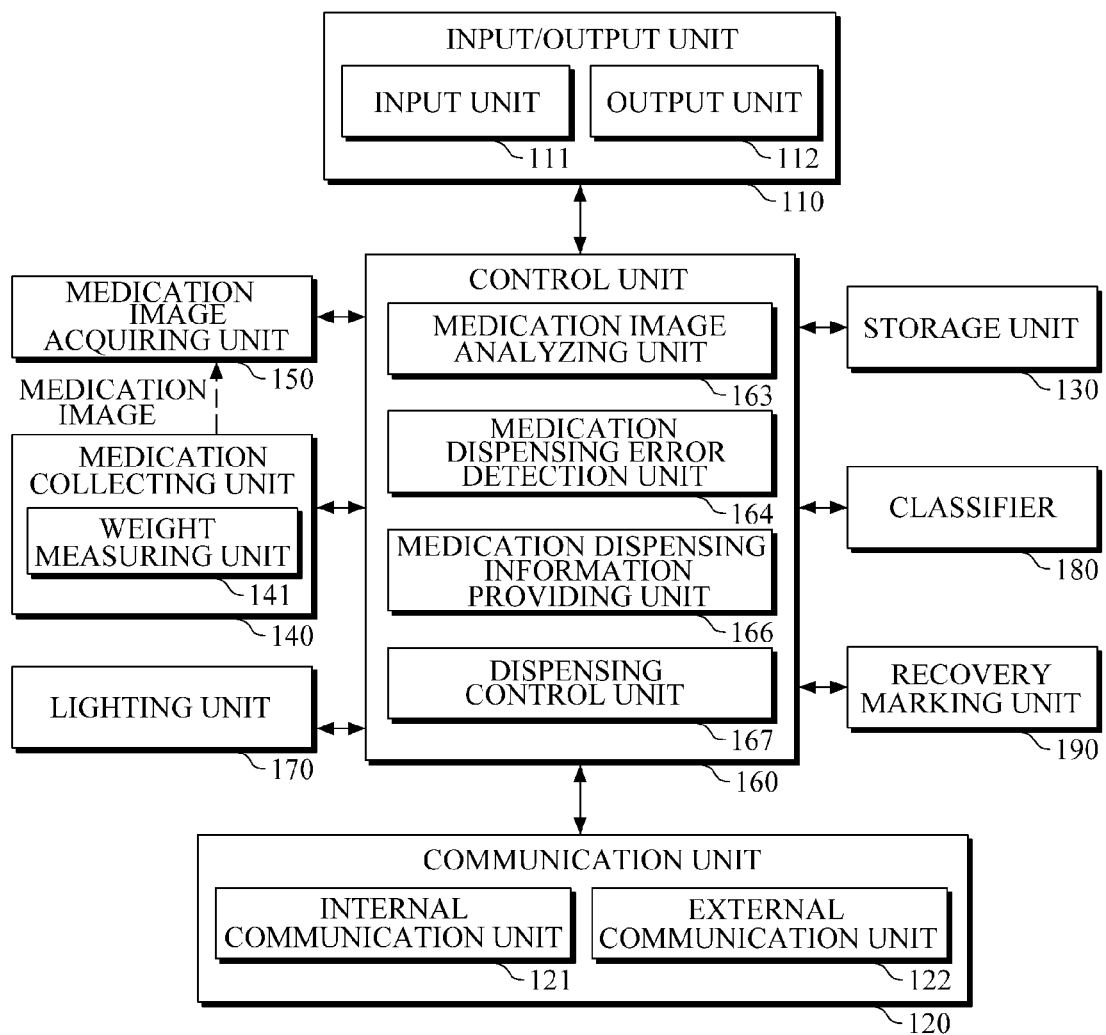
FIG. 18 is a block diagram illustrating a medication dispensing apparatus according to yet another exemplary embodiment of the present invention.

FIG. 18 is a block diagram illustrating a medication dispensing apparatus according to yet another exemplary embodiment of the present invention.

The medication dispensing apparatus illustrated in 18 is the same as the medication dispensing apparatus of FIG. 5, except for the control unit 160. Referring to FIG. 18, the control unit 160 may include a medication image analyzing unit 163, a medication dispensing error detection unit 164, a medication dispensing information providing unit 166, and a dispensing control unit 167. A medication image analyzing unit 163 and medication dispensing error detection unit 164 of FIG. 18 are the same as those illustrated in FIG. 5. A medication dispensing information providing unit 166 and dispensing control unit 167 of FIG. 8 are different from the dispensing control unit 162 of FIG. 5. The medication dispensing information providing unit 166 may provide to the user information on prescribed medication, medication image information, and determination data obtained by the medication dispensing error detection unit 164. In one example, the medication dispensing information providing unit 166 may output the received information and data to the display unit 122. In another example, the medication dispensing information providing unit 164 may transmit the received information and data to an external communication device through an external communication unit 122. The external communication device may be the manager server 200. Accordingly, the user may visually check the occurrence of medication dispensing error by means of the display unit 112, or the external communication device.

The dispensing control unit 167 may control the dispensing process to be continued or control the medication to be re-dispensed according to the user's input or the determination made by the medication dispensing error detection unit 164. In one example, the dispensing control unit 167 may continue to perform the dispensing process or control the medication to be re-dispensed, either in response to the user's input when in "user mode," or according to the determination made by the medication dispensing error detection unit 164 when in "automatic mode." The user may choose the "user mode" or the "automatic mode." When the user wishes to conduct a visual check to detect the medication dispensing error, the user may set the mode of the apparatus to "user mode" through the input/output unit 110. When wishing to automatically dispense the medication, the user may set the mode to "automatic mode" through the input/output unit 110. In "automatic mode," the user is enabled to monitor the medication image, information on prescribed medication, and data related to determination on medication dispensing error through the display unit 112, and thus can check whether the automatic dispensing process is performed normally. Other than the elements described above, the remaining elements of FIG. 18 are the same as those in FIGS. 5 and 17, and thus detailed descriptions thereof will not be reiterated.

According to the exemplary embodiments, the medication dispensing apparatus photographs an image of medications for one dose, which are collected from cartridges and contained in the collecting unit, and provides to a user the photographed medication image and prescription information, based on which the user determines whether a medication dispensing error occurred. Therefore, it is possible to almost completely prevent erroneous dispensing. In addition, this apparatus is complies with the legal standards that require a pharmacist to conduct dispensing inspection.

Moreover, the medication dispensing apparatus analyzes the photographed medication image to determine whether there is an error in medication dispensing, and then provides the determination to the user, so that the user can easily perform dispensing inspection.

Additionally, the medication dispensing apparatus automatically recovers erroneously dispensed medications or makes them more noticeable for the user to easily distinguish the erroneous medications.

Further, the medication dispensing apparatus photographs an image of medications for one dose, which are collected from the cartridges and contained in the collecting unit, then analyzes the photographed medication image, and automatically continues to perform the dispensing process, or controls the medications to be re-dispensed according to the analysis result. Accordingly, it is possible to prevent the medication dispensing error, and to increase the user's convenience of use.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented with other components or their equivalents. Accordingly, other implementations are within the scope of the following claims.

What is claimed is:

1. A medication dispensing apparatus for preventing a medication dispensing error, comprising:

a communication unit configured to communicate with a manager server;

a medication collecting unit configured to gather capsules or tablets for one dose that are discharged from cartridges;

a medication image acquiring unit configured to acquire an image of the capsules or tablets contained in the medication collecting unit; and a control unit configured to comprise a dispensing information delivery unit to transmit to the manager server the medication information acquired by the medication image acquiring unit, and a dispensing control unit to continue a medication dispensing process or control capsules or tablets to be re-dispensed according to a user's dispensing control instruction received from the manager server, in response to the image being acquired and transmitted to the manager server.

2. The medication dispensing apparatus of claim 1, wherein the control unit further comprises a medication image analyzing unit to analyze the acquired medication image, and a medication dispensing error determining unit to determine an occurrence of a medication dispensing error based on an analysis result from the image analyzing unit, and the dispensing information delivery unit may transmit to the manager server a determination made by the medication dispensing error detection unit.

3. The medication dispensing apparatus of claim 2, wherein the medication image analyzing unit analyzes at least one factor of the pills' numbers, shapes, colors and sizes within the acquired medication image.

4. The medication dispensing apparatus of claim 1, further comprising:
a classifier configured to classify the medications from the medication collection unit to be either in a recovery area or in a packaging area.

5. The medication dispensing apparatus of claim 1, further comprising:
a recovery marking unit configured to mark a package of capsules or tablets which are discharged from the medication collecting unit and are subject to recovery.

6. The medication dispensing apparatus of claim 5, wherein the recovery marking unit is a punch unit.

7. A medication dispensing apparatus for preventing a medication dispensing error, comprising:

a medication collecting unit configured to contain capsules or tablets for one dose which are discharged from cartridges and to discharge the contained capsules or tablets to a packaging unit;

a medication image acquiring unit configured to acquire an image of the capsules or tablets contained in the medication collecting unit; and a control unit configured to comprise a medication image analyzing unit to analyze the image acquired by the medication image acquiring unit, a medication dispensing error detection unit to determine an occurrence of a medication dispensing error based on an analysis result from the medication image analyzing unit, a medication dispensing information providing unit to provide to a user information on prescribed medication, the medication image acquired by the medication image acquiring unit and a determination made by the medication dispensing error detection unit, and a dispensing control unit to continue a medication dispensing process or control capsules or tablets to be re-dispensed according to a user's input or the determination made by the medication dispensing error detection unit, in response to the image being acquired and transmitted to the manager server.

8. The medication dispensing apparatus of claim 7, further comprising:
a display unit;
wherein the medication dispensing information providing unit outputs to the display unit the medication image acquired by the medication image acquiring unit and the determination made by the medication dispensing error detection unit.

9. The medication dispensing apparatus of claim 7, wherein the dispensing control unit continues the medication dispensing process, or controls capsules or tablets to be re-dispensed, according to a user's input in user mode, or according to the determination made by the medication dispensing error detection unit in automatic mode.

10. The medication dispensing apparatus of claim 7, wherein the medication image analyzing unit analyzes at least one factor of the pills' numbers, shapes, colors, and/or sizes within the acquired medication image.

11. The medication dispensing apparatus of claim 10, further comprising:
a weight measuring unit configured to measure a total weight of the capsules or tablets contained in the medication collecting unit,
wherein the medication dispensing error detection unit takes into consideration the measured weight to determine the occurrence of medication dispensing error.

12. The medication dispensing apparatus of claim 7, further comprising:
a classifier configured to classify the medications from the medication collection unit to be either in a recovery area or in a packaging area.

13. The medication dispensing apparatus of claim 7, further comprising:
a recovery marking unit configured to mark a package of capsules or tablets which are discharged from the medication collecting unit and are subject to recovery.

14. The medication dispensing apparatus of claim 13, wherein the recovery marking unit is a punch unit 2.

* * * * *